United States Patent [19]

Task et al.

[11] Patent Number: 4,461,570
[45] Date of Patent: Jul. 24, 1984

[54] METHOD FOR DYNAMICALLY RECORDING DISTORTION IN A TRANSPARENCY

[75] Inventors: Harry L. Task, Dayton; Louis V. Genco, Enon, both of Ohio

[73] Assignee: The United States of America as represented by the Secretary of the Air Force, Washington, D.C.

[21] Appl. No.: 386,488

[22] Filed: Jun. 9, 1982

[51] Int. Cl.$^3$ ............................................ G01N 21/00
[52] U.S. Cl. ..................................... 356/239; 356/389
[58] Field of Search ............... 356/124, 127, 389, 398, 356/239, 240, 371

[56] References Cited

U.S. PATENT DOCUMENTS

| 4,099,877 | 7/1978 | Brouwer | 356/124 |
| 4,299,482 | 11/1981 | Task | 356/124 |

FOREIGN PATENT DOCUMENTS

| 1116748 | 6/1968 | United Kingdom | 356/398 |
| 1407812 | 9/1975 | United Kingdom | |

OTHER PUBLICATIONS

Hammond et al., "Detecting Surface Deformities," *IBM Tech. Disclo. Bull.*, vol. 14, No. 1, pp. 49–50, Jun. 1971.
Herman et al., "Methods and Apparatus for Detecting Deviations from Planarity," *Technical Digest*, pub. by Western Electric, " No. 44, pp. 27–28, Oct. 1976.
Genco, Louis V. and Task, Harry L., "Aircraft Transparency Optical Quality: New Methods of Measurement," Feb. 1981, Report No. AFAMRL-TR-81-21.
Self, Hershel C. and Task, Harry L., "Potential of Optical Analysis for Measuring Windscreen Distortion," Dec. 1980, Report No. AFAMRL-TR-80-104.

*Primary Examiner*—William L. Sikes
*Assistant Examiner*—Matthew W. Koren
*Attorney, Agent, or Firm*—Donald J. Singer; John R. Flanagan

[57] ABSTRACT

A method for dynamically recording distortion in a transparency includes a support fixture for mounting the transparency for movement about a predetermined horizontal or vertical axis, with a camera disposed in back of the transparency while a test target is disposed in front of it. The test target has a plurality of small light sources arranged in a rectangular matrix pattern toward which the camera is aimed through the transparency. By opening the camera shutter for a period of time as the transparency is moved through a predetermined angle, a photographic record of distortion at a plurality of regions in the transparency is produced.

6 Claims, 7 Drawing Figures

METHOD FOR DYNAMICALLY RECORDING DISTORTION IN A TRANSPARENCY

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to optical defects in transparencies and, more particularly, is concerned with a dynamic distortion recording method utilizing photographic time exposure techniques to record the "distortion track" of a test target pattern observed through a moving transparency, such as an aircraft windscreen.

2. Description of the Prior Art

As a general rule, optically transparent, asymmetrically contoured bodies have been difficult to quantitatively evaluate and compare on the basis of their optical characteristics. A prime example of a structural element formed of a transparent medium in which optical quality is critical, yet difficult to quantitatively evaluate, is the canopy or windscreen of aircraft having complex curvilinear contours.

Distortion is one of the optical quality parameters that has been identified for characterizing transparencies, such as aircraft windscreens. Distortion is the nonlinear mapping of object points to image space due to the optical effects of the transparency. Such effects may be due to either optical index variations in the transparency or to the opposite faces of the transparency being non-parallel.

Heretofore aircraft windscreens have been measured while stationary and by using static test targets and photographic techniques. Several windscreen distortion, static measuring methods are described in Air Force Aerospace Medical Research Laboratory Report No. AFAMRL-TR-81-21, dated February 1981. Also, windscreens are inspected visually for distortion by inspectors that bob their heads to observe the effects of dynamic distortion, that is, distortion produced in the image of an object as viewed through the windscreen when the object and windscreen are moving relative to one another. This inspection technique, being very crude and subjective, is not amenable to standardization, nor preparation of an objective record of the degree of distortion observed by the inspector.

Consequently, a need exists for a technique to record dynamic distortion in transparencies, such as aircraft windscreens, in a way which will facilitate establishment of pass-fail type criteria for use in production inspection or comparison of windscreens.

SUMMARY OF THE INVENTION

The present invention provides a dynamic distortion recording method designed to satisfy the aforementioned needs. The unique feature of the present invention is the use of a photographic time exposure technique to record the "distortion track" created by a dot matrix target pattern of lights being photographically observed through a moving transparency. By the use of a dot matrix pattern and as a result of photographic time exposure of the pattern through the moving transparency, such as an aircraft windscreen, a "hard copy" recording of distortion at a plurality of regions in the transparency may be produced. Such hard copy recording simulates the image which would be seen by inspectors when bobbing their heads to observe the effects of distortion in the transparency.

The advantages of a hard copy recording over a subjective, momentary evaluation by an inspector are readily apparent. A physical record containing one approach to appraising the optical quality of the transparency is produced. The physical record may be compared with similar records taken of other transparencies for establishing a pass-fail type of standard. Furthermore, a record is obtained for archival purposes on each particular transparency. No such objective historical data may be obtained using the aforementioned visual inspection technique.

Accordingly, the present invention is directed to a method for dynamically recording distortion in a transparency, which includes the operative steps of: (a) mounting the transparency for movement about a predetermined axis; (b) disposing a test target at one side of the transparency; (c) disposing a camera at a side of the transparency opposite to the one side thereof; (d) aiming the camera toward the test target so as to place a plurality of small target elements, mounted thereon in a predetermined array, within its field of view through the transparency; and (e) opening a shutter of the camera for a predetermined period of time as the transparency is moved through a predetermined angle over the same period of time such that a photographic record of distortion at a plurality of regions in the transparency is produced. The target elements preferably take the form of a plurality of lights arranged in a rectangular grid-like matrix.

DETAILED DESCRIPTION OF THE INVENTION

Figure 1:
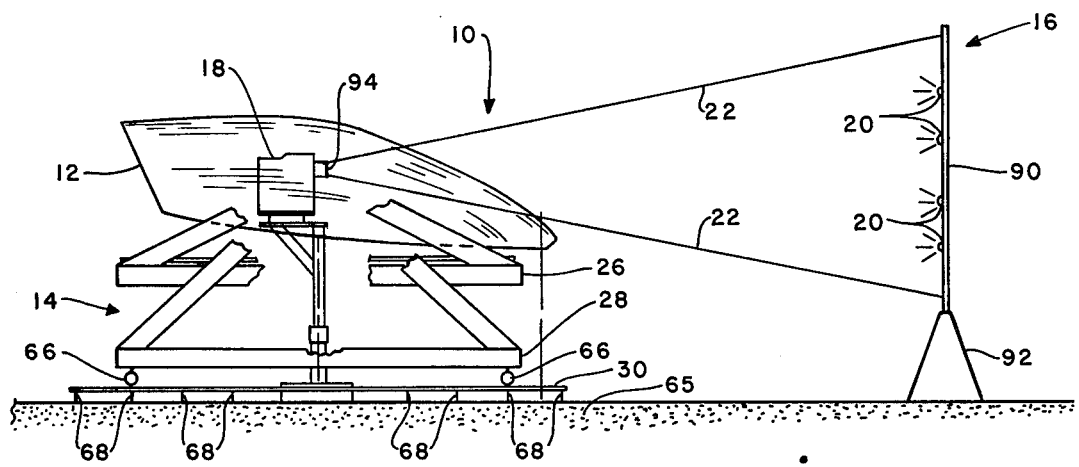
FIG. 1 is a schematic view, partially broken away, of the system for carrying out the method of the present invention for dynamically recording distortion in a transparency.
Figure 7:
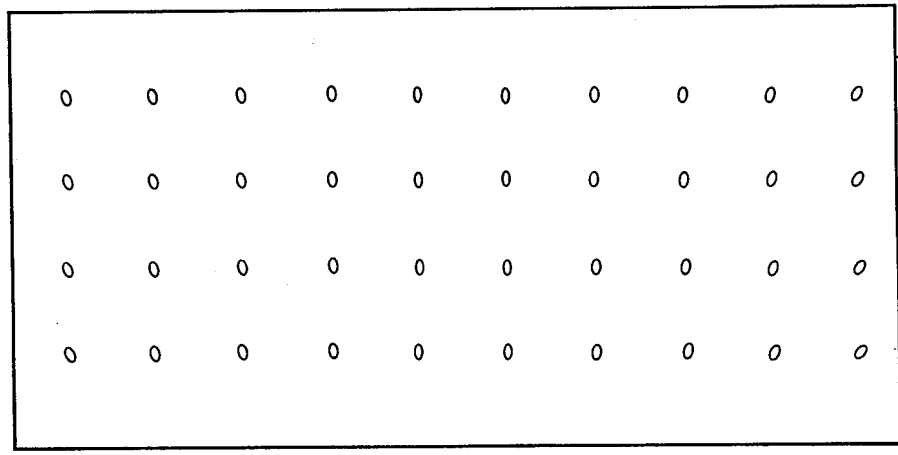
FIG. 7 is an example of a photographic recording of a distortion track produced as a result of the dynamic distortion test performed on a transparency in accordance with the system and method of the present invention.
Figure 4:
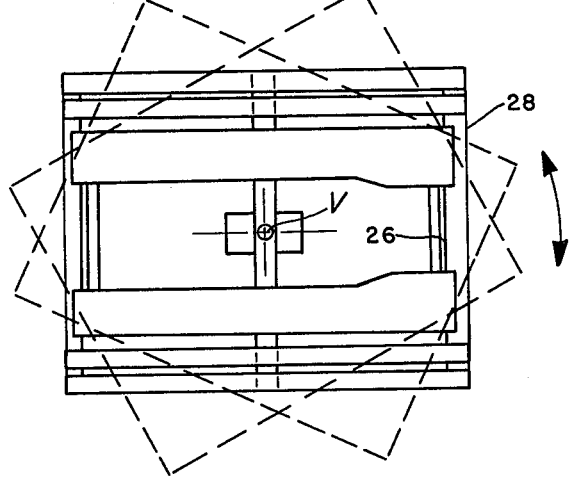
FIG. 4 is a top plan view of the platform and a table mounted thereon, on a slightly smaller scale than that of FIG. 1, showing examples of the angular positions, in broken line form, to which the platform and table therewith may be rotated about a vertical axis.
Figure 5:
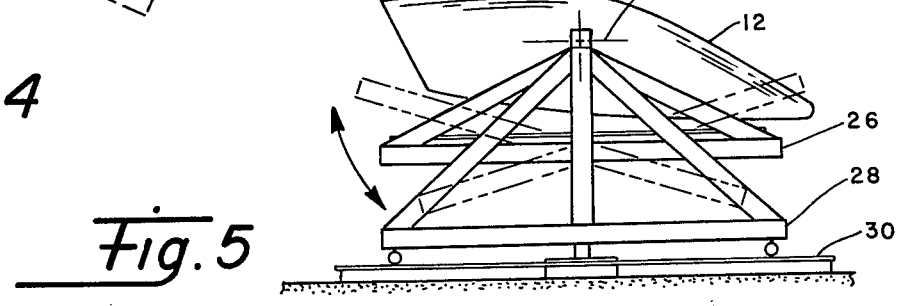
FIG. 5 is a side elevational view, on the same scale as that of FIG. 4, of the platform and table, showing examples of the angular positions, in broken line form, to which the table may be pivoted about a horizontal axis.

Referring now to the drawings, and more particularly to FIG. 1, there is shown, in partially broken away schematical form, a system, generally designated 10, for dynamically recording distortion in a transparency 12, such as an aircraft windscreen or the like. The system 10 includes a support fixture 14, a test target 16, and a camera 18. The support fixture 14 mounts the transparency 12 for movement about a vertical axis V (FIG. 4) and a horizontal axis H (FIG. 5). The test target 16 is disposed at one side, such as the front side, of the transparency 12, while the camera 18 is disposed at a side, such as the back side, of the transparency 12 opposite to the one, or front, side thereof. The test target 16 includes a plurality of small target elements, preferably in the form of light sources 20, which are arranged in a predetermined array, such as a rectangular dot matrix target pattern. The camera 18 is aimed toward the test target 16 so as to contain the array of target light sources 20 within its field of view, as represented by the region between lines 22 of FIG. 1. Then, by operating the camera in a conventional time exposure mode, such as by opening the shutter (not shown) of the camera, for a predetermined period of time as the transparency is moved through a predetermined angle over the same period of time, a photographic record 24, such as seen in FIG. 7, of distortion at a plurality of regions in the transparency 12 may be produced.

Figure 2:
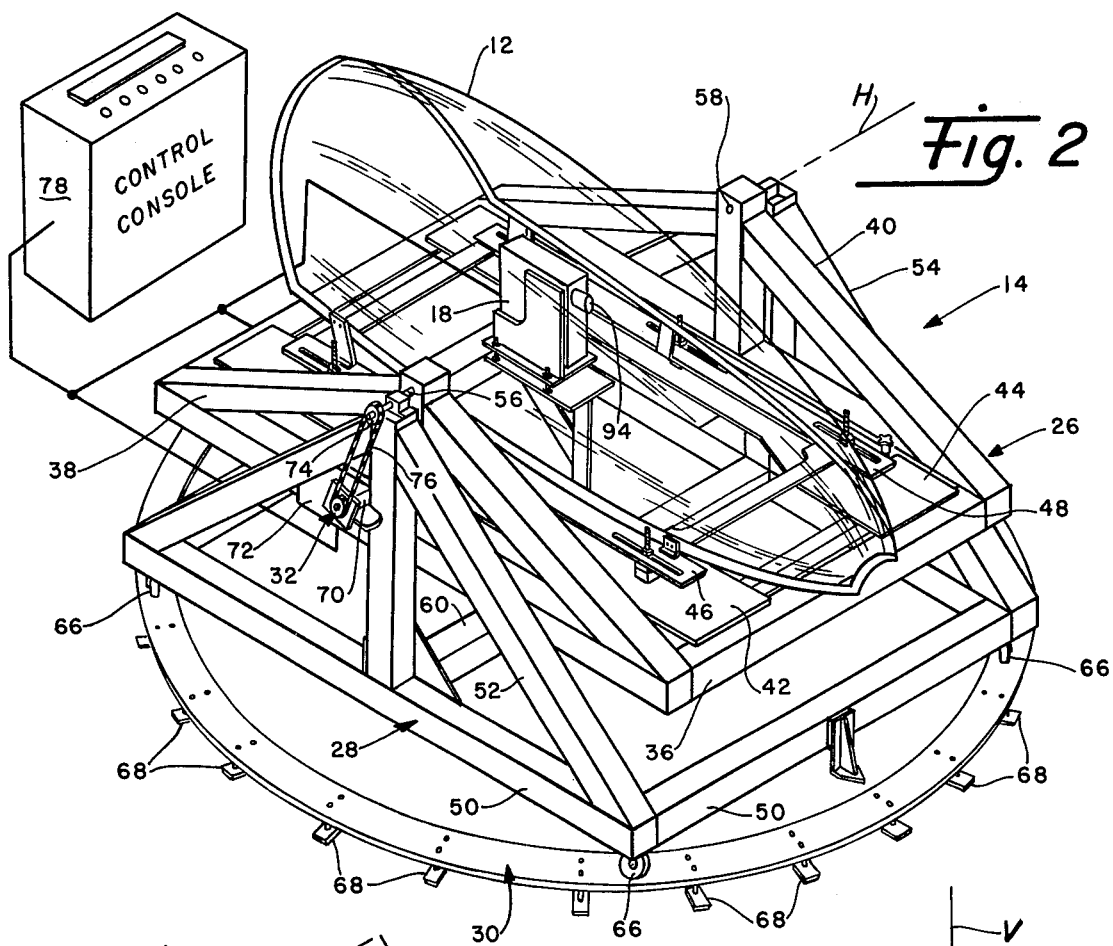
FIG. 2 is an enlarged perspective view of a portion of the dynamic distortion recording system of FIG. 1.
Figure 3:
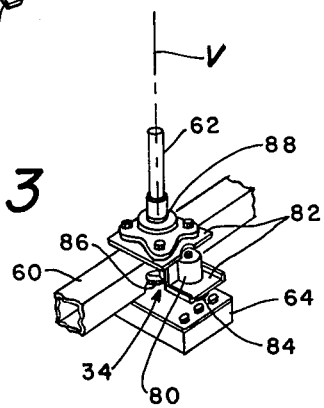
FIG. 3 is a fragmentary perspective view of drive means for rotating a platform of the recording system, which drive means is hidden in the view of FIG. 1.

In an exemplary embodiment more clearly seen in FIG. 2, the support fixture 14 basically includes a table 26, platform 28, track 30, first drive means 32, and second drive means 34. The platform 28 pivotally mounts the table 26 about the horizontal axis H. The track 30 supports the platform 28 for rotational movement about the vertical axis V (FIG. 3). The first drive means 32 is operable for causing pivoting of the table 26 relative to the platform 28 about horizontal axis H, while the second drive means 34 is operable for causing rotation of the platform 28 about the track 30.

The table 26 is composed of a rectangular frame structure 36 with upstanding hanger trusses 38, 40 attached along the lateral sides thereof. Laterally spaced apart support plates 42, 44 are attached to the rectangular frame structure 36 for affixing the transparency 12 at a desired position on the table 26 via adjustable bracket structures 46, 48.

The platform 28 is formed by a base frame 50 with upright trusses 52, 54 attached at opposite sides thereof adjacent the hanger trusses 38, 40 of the table 26. At the upper apexes of the adjacent hanger and upright trusses 38, 52 and 40, 54, the table 26 is mounted to the platform 28 by axially aligned shafts 56, 58 which define the horizontal axis H. The platform 28, in turn, is rotatably journaled at the mid-section of a cross beam 60 of its base frame 50 to an upright support pedestal 62 (FIG. 3) for the camera 18 which is attached by a block 64 to the floor 65 of the facility which houses the system 10. The support pedestal 62 defines the vertical axis V about which the platform 28 rotates on the track 30 relative to the pedestal 62 and upon four rollers 66 supporting the platform 28 below the four corners of its base frame 50.

The track 30 is of circular configuration and supported on mounting brackets 68 which are attached to the floor 65 (FIG. 2) of the facility. The brackets are individually adjustable for raising and lowering contiguous parts of the track in order to place it in a level, horizontal condition.

For moving the table 26 relative to the platform 28, the first drive means 32 includes an electric motor 70 mounted to the right upright truss 52 of the platform 28 by a plate 72, and a pair of gear sprockets 74 and a drive chain 76 which interconnect, and transmit the motion of, the motor 70 to the right shaft 56 which is fixed to the right hanger truss 38 of the table 26. By selective operation of the motor 70 through manipulation of suitable controls at a control console 78, the table 26 and the transparency 12 therewith are caused to pivot about horizontal axis H through a predetermined angle, such as 20 degrees, relative to the platform 28. Examples of angular displacements of the table 26 from the horizontal plane are shown in FIG. 5. The control console is only shown in diagrammatic form since it forms no part of the present invention. Many different conventional control devices for simultaneously opening the shutter of the camera 18 and moving the transparency 12 will be within the purview of those skilled in the art.

For moving the platform 28 about the track 30, the second drive means 34, clearly shown in FIG. 3, includes an electric motor 80 mounted by a bracket 82 affixed to the cross beam 80 of the platform base frame 50. The motor 80 has a small drive sprocket gear 84 which intermeshes with a large sprocket gear 86 attached to a stationary shaft 88 below the cross beam 60. As the small drive gear 84 is rotated by selective operation of the motor 80 through manipulation of controls at the control console 78, it concurrently revolves about the vertical axis V of shaft 88 and moves along the periphery of stationary gear 86. Such rotation and revolution of gear 84 causes rotation of the platform 28, and the table 26 and transparency 12 therewith, about the vertical axis V through a predetermined angle, such as 20 degrees, relative to the track 30. Examples of angular displacement of the platform 28 and table 26 are shown in FIG. 4.

As seen in FIGS. 1 through 3, the camera 18 is mounted on the upright support pedestal 62 in back of the transparency 12. The pedestal 62 is positioned to extend upwardly through the table 26 and platform 28 irrespective of their angular positions. It will be noted that the camera is disposed generally at the intersection of the horizontal and vertical axes of table movement. Also, there is no cross bar on the table to contact the pedestal upon pivotal movement of the table 26. Finally, the pedestal at its lower end is connected to shaft 88 to which the cross beam 60 of the platform 28 is rotatably journaled and which shaft 88 is attached to the floor 65 by block 64. Therefore, it should be apparent that no part of the camera and its support pedestal will obstruct or interfere with the potential paths of movement of the platform 28, table 26 and transparency 12.

As seen in FIG. 1, the test target 16 is mounted in front of the transparency 12. The test target 16 includes the aforementioned matrix of light sources 20 which are mounted on a rectangular board 90 which, in turn, is supported above the facility floor 65 by a base 92. The board 90 faces the camera 18 through the transparency 12 such that the matrix of light sources 20 are contained within the field of view 22 of the camera lens 94, being positioned at the design eye of the transparency 12 which also coincides with the intersection of the horizontal and vertical axes H, V. The design eye of the transparency refers to the location of the eyes of the occupant of the vehicle to which the transparency will be attached. Depending upon the particular configuration of transparency and location of the observer in relation to it, the design eye position and thus the axes of movement of the transparency may be at some other position relative to the transparency than the one shown in FIGS. 1 and 2.

Figure 6:
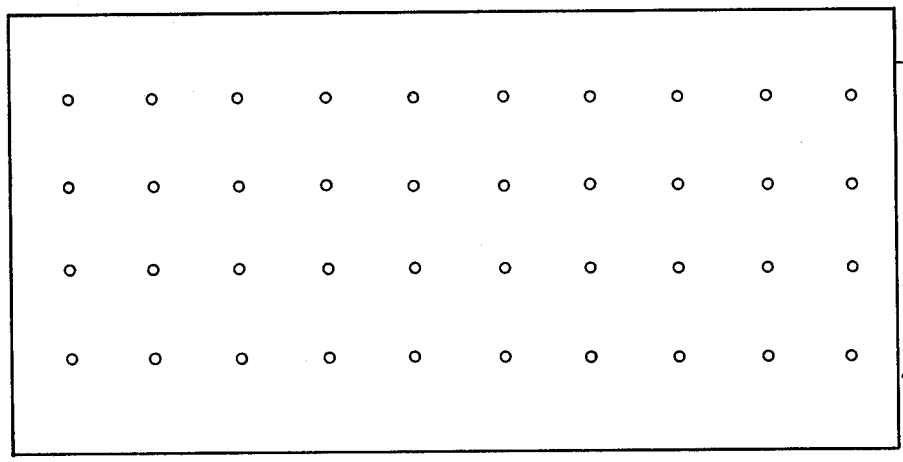
FIG. 6 is an example of a photographic recording of the test target of the system, showing the rectangular matrix pattern or array of small lights prior to testing of a transparency for distortion.

To recap, the transparency 12 is mounted on a support fixture 14 for rotational or pivotal movement about either vertical or horizontal axes which intersect at the design eye position or any other designated observer view point through the transparency 12. The transparency 12, support fixture 14, test target 16 and camera 18 are preferably all located in a dark room. The test target 16 which mounts small circular light sources 20 in a rectangular matrix pattern or array is within the field of view of the camera lens 94 through the transparency 12. As the camera shutter (not shown) is opened, the transparency is moved about a predetermined one of the axes through a predetermined angle or distance, after which the camera shutter is closed. In other words, the camera is operated in a time exposure mode for a predetermined time period which is the same as the period of time over which the transparency is moved through the predetermined angle. If no distortion is present, the resulting photographic record 24 will show only the rectilinear array of light sources, as represented by the small circular dots seen in FIG. 6. However, if some distortion is present, the photographic record will show "distortion tracks." These tracks result from the light rays passing through different portions of the transparency during the period of the time exposure and the varied angular deviations suffered by the rays at the different parts or regions of the transparency. An example of a photographic record 24 of distortion produced at a plurality of regions in a transparency is represented by the irregular, elongated-shaped dots in FIG. 7. The greater the excursions of the tracks from the small circular dots of FIG. 6 the more severe the degree of distortion in that particular region of the transparency.

It is thought that the present invention and many of the attendant advantages thereof will be understood from the foregoing description and it will be apparent that various changes may be made in the parts thereof without departing from the spirit and scope of the invention or sacrificing all of its material advantages, the form hereinbefore described being merely a preferred or exemplary embodiment thereof.

Having thus described the invention, what is claimed is:

1. A method for dynamically recording distortion in a transparency, comprising the steps of:
    (a) mounting said transparency for movement about a predetermined axis;
    (b) disposing a test target at one side of said transparency, said test target having a plurality of small target elements mounted thereon in a predetermined array;
    (c) disposing a camera at a side of said transparency opposite to said one side thereof;
    (d) aiming said camera toward said test target so as to place said array of target elements within its field of view through said transparency; and
    (e) operating said camera in a time exposure mode for a predetermined period of time as said transparency is moved through a predetermined angle over the same period of time such that a photographic record of distortion at a plurality of regions in said transparency is produced.

2. The dynamic distortion recording method as recited in claim 1, wherein said predetermined axis is aligned in a generally horizontal direction.

3. The dynamic distortion recording method as recited in claim 1, wherein said predetermined axis is aligned in a generally vertical direction.

4. The dynamic distortion recording method as recited in claim 1, wherein said camera is disposed generally at the predetermined axis of movement of said transparency.

5. The dynamic distortion recording method as recited in claim 1, wherein said camera is disposed at a design eye position of said transparency.

6. The dynamic distortion recording method as recited in claim 1, wherein said plurality of small target elements comprises a plurality of light sources arranged in a rectangular matrix pattern.

* * * * *